(12) United States Patent
Brand (10) Patent No.: US 7,476,388 B2
(45) Date of Patent: Jan. 13, 2009

(54) COMPOSITION COMPRISING A GASTRIN/CCK RECEPTOR LIGAND AND AN EGF RECEPTOR LIGAND

(75) Inventor: Stephen J. Brand, Lincoln, MA (US)

(73) Assignee: Waratah Pharmaceuticals, Inc., Verden (CA)

( * ) Notice: Subject to any disclaimer, the term of this patent is extended or adjusted under 35 U.S.C. 154(b) by 15 days.

(21) Appl. No.: 11/273,615

(22) Filed: Nov. 14, 2005

(65) Prior Publication Data

US 2006/0234932 A1    Oct. 19, 2006

Related U.S. Application Data

(63) Continuation of application No. 10/044,048, filed on Jan. 11, 2002, now Pat. No. 6,992,060.

(60) Provisional application No. 60/261,638, filed on Jan. 12, 2001.

(51) Int. Cl.
*A61K 38/16* (2006.01)
*A61K 38/18* (2006.01)
*C07K 14/475* (2006.01)
*C07K 14/595* (2006.01)

(52) U.S. Cl. ............... 424/198.1; 424/184.1; 530/300; 530/350; 530/399; 514/2; 514/12; 435/810; 435/975

(58) Field of Classification Search .......... None
See application file for complete search history.

(56) References Cited

U.S. PATENT DOCUMENTS

| | | | |
|---|---|---|---|
| 3,917,824 A | 11/1975 | Camble et al. | 424/177 |
| 4,686,283 A | 8/1987 | Nestor, Jr. et al. | 530/327 |
| 4,760,023 A | 7/1988 | Miyoshi et al. | |
| 5,158,935 A | 10/1992 | Nascimento et al. | |
| 5,189,049 A | 2/1993 | Frehel et al. | 514/371 |
| 5,885,956 A | 3/1999 | Nardi et al. | |
| 6,288,301 B1 | 9/2001 | Nardi et al. | |
| 6,326,201 B1 | 12/2001 | Fung et al. | 435/377 |
| 6,558,952 B1 | 5/2003 | Parikh et al. | 435/384 |
| 6,899,883 B2 | 5/2005 | Dupre | 424/198.1 |
| 6,989,148 B2 | 1/2006 | Dupre | 424/198.1 |
| 6,992,060 B2 | 1/2006 | Brand | 514/2 |
| 7,202,080 B2 | 4/2007 | Ramiya et al. | 435/325 |
| 2002/0081285 A1 | 6/2002 | Parikh et al. | 424/93.21 |
| 2002/0119146 A1 | 8/2002 | Dupre | 424/139.1 |
| 2002/0182728 A1 | 12/2002 | Ramiya et al. | 435/366 |
| 2003/0171269 A1 | 9/2003 | Magil et al. | 514/12 |
| 2004/0023885 A1 | 2/2004 | Brand et al. | 514/12 |
| 2004/0037818 A1 | 2/2004 | Brand et al. | 424/93.21 |
| 2004/0209801 A1 | 10/2004 | Brand et al. | 514/12 |
| 2004/0209816 A1 | 10/2004 | Parikh et al. | 514/12 |
| 2004/0229810 A1 | 11/2004 | Cruz | 514/14 |
| 2004/0266682 A1 | 12/2004 | Cruz | 514/12 |
| 2006/0183674 A1 | 8/2006 | Brand et al. | 514/11 |
| 2006/0189520 A1 | 8/2006 | Brand et al. | 514/12 |
| 2006/0234373 A1 | 10/2006 | Rabinovitch et al. | 435/325 |
| 2006/0234932 A1 | 10/2006 | Brand | 514/12 |

FOREIGN PATENT DOCUMENTS

| | | |
|---|---|---|
| EP | 0 161 816 A2 | 11/1985 |
| WO | WO 90/10697 | 9/1990 |
| WO | WO 90/13570 | 11/1990 |
| WO | WO 93/03757 | 3/1993 |
| WO | 93/14783 | 8/1993 |
| WO | WO 95/19785 | 7/1995 |
| WO | WO 95/31214 | 11/1995 |
| WO | WO 00/29438 | 5/2000 |
| WO | WO 00/44400 | 8/2000 |
| WO | WO 02/12452 A2 | 2/2002 |
| WO | WO 02/055152 A2 | 7/2002 |
| WO | WO 03/040310 A2 | 5/2003 |
| WO | WO 03/100024 A2 | 12/2003 |
| WO | WO 03/103701 A1 | 12/2003 |
| WO | WO 2004/037195 A2 | 5/2004 |
| WO | WO 2004/045640 A1 | 6/2004 |
| WO | WO 2004/096583 A1 | 11/2004 |
| WO | WO 2004/105780 A2 | 12/2004 |
| WO | WO 2005/072045 A2 | 8/2005 |
| WO | WO 2006/002532 A1 | 1/2006 |

(Continued)

OTHER PUBLICATIONS

Ahmed et al., "High and Low Affinity Receptors Mediate Growth Effects of Gastrin and Gastrin-Gly on DLD-1 Human Colonic Carcinoma Cells", *FEBS Letters*, 556:199-203 (2004).

(Continued)

*Primary Examiner*—Bridget E Bunner
(74) *Attorney, Agent, or Firm*—Erica R. Carlson; Ivor E. Elrifi; Mintz, Levin, Cohn, Ferris, Glovesky and Popeo PC (57) ABSTRACT

Compositions and methods are provided for achieving in vivo islet cell regeneration in subjects with preexisting diabetes. The methods comprise short term treatment with a composition having a gastrin/cholecystokinin receptor ligand and an EGF receptor ligand. Treatment with such a composition for a short term resulted in a prolonged period of increased insulin release, decreased fasting blood glucose, and improved glucose tolerance, the prolonged efficacy, the period being considered from the time of cessation of treatment.

11 Claims, 6 Drawing Sheets

FOREIGN PATENT DOCUMENTS

| | | |
|---|---|---|
| WO | WO 2007/041833 A1 | 4/2007 |
| WO | WO 2007/062531 A1 | 6/2007 |
| WO | WO 2007/095737 A1 | 8/2007 |

OTHER PUBLICATIONS

Araki et al., "Stability of Recombinant Epidermal Growth Factor in Various Solutions", *Chem. Pharm. Bull.*, 37(2):404-406 (1989).
Baggio et al., "Therapeutic approaches to preserve islet mass in type 2 diabetes", *Annual Review of Medicine*, 57:265-281 (2006).
Bérubé et al., "Effects of Cerulein and Epidermal Growth Factor on Pancreatic Growth in the Reserpinized Rat Model", *J. of Pediatric Gastroenterology and Nutrition*, 17:39-48 (1993).
Brand et al., "Pharmacological Treatment of Chronic Diabetes by Stimulating Pancreatic b-Cell Regeneration with Systemic Co-administration of EGF and Gastrin", *Pharmacology & Toxicology*, 91(6):414-420 (2002).
Brand et al., "Prolonged Efficacy of Islet Neogenesis Therapy with Gastrin and TGFα in Mature Rats with Preexisting Diabetes", *Diabetes*, 50(Suppl 2):338 (Abstract) (2001).
Calnan et al., "Potency and Stability of C Terminal Truncated Human Epidermal Growth Factor", *Gut*, 47:622-627 (2000).
Campbell et al., "Structure-function relationships in epidermal growth factor (EGF) and transforming growth factor-alpha (TGF-alpha)", *Biochem. Pharmacol.*, 40(1):35-40 (1990).
Carver et al., "A high resolution 1H NMR study of the solution structure of human epidermal growth factor", *FEBS Lett.*, 205:77-81 (1986).
Clare et al., "Production of Mouse Growth Factor in Yeast: High-Level Secretion Using *Pichia pastoris* Strains Containing Multiple Gene Copies", *Gene*, 105(1):205-212 (1991).
Conteas et al., "The Effects of Gastrin, Epidermal Growth Factor, and Somatostatin on DNA Synthesis in a Small Intestinal Crypt Cell Line (IEC-6) (42484)", *Proc. Soc. Exp. Biol. Med.*, 184(3):307-311 (1987).
Cooke et al., "The solution structure of human epidermal growth factor", *Nature*, 327:339-341 (1987).
Cras-Meneur et al., "Epidermal growth factor increases undifferentiated pancreatic embryonic cells in vitro: a balance between proliferation and differentiation", *Diabetes*, 50:1571-1579 (2001).
Crean et al., "Parietal cell hyperplasia induced by the administration of pentagastrin (ICI 50,123) to rats", *Gastroenterology*, 57(2):147-55 (1969).
Creutzfeldt et al., "Is hypergastrinaemia dangerous to man?", *Scand J Gastroenterol Suppl.*, 180:179-191 (1991).
Datta et al., "Ionizing radiation activates transcription of the EGRI gene via CArG elements", *Proc. Natl. Acad. Sci.* USA, 89:10149-10153 (1992).
Dembinski et al., "Trophic Action of Epidermal Growth Factor on the Pancreas and Gastroduodenal Mucosa in Rats", *J Physiol (Lond)*, 325:35-42 (1982).
Di Lorenzo et al., "Involvement of growth factor receptors of the epidermal growth factor receptor family in prostate cancer development and progression to androgen independence", *Clin. Prostate Cancer*, 2(1):50-57 (2003).
DiAugustine et al., "Evidence for Isoaspartyl (Deamidated) Forms of Mouse Epidemal Growth Factor", *Analytical Biochemistry*, 165:420-429 (1987).
Drumm et al., "Urogastrone/epidermal growth factor in treatment of congenital microvillous atrophy", *Lancet*, 1(8577):111-112 (1988).
Efrat, S., "Prospects for gene therapy of insulin-dependent *diabetes mellitus*", *Diabetologia*, 41:1401-1409 (1998).
Ferrara et al., "Molecular and Biological Properties of the Vascular Endothelial Growth Factor Family of Proteins", *Endocr Rev*, 13(1):18-32 (1992).
George-Nascimento et al., "Characterization of Recombinant Human Epidermal Growth Factor Produced in Yeast", *Biochemistry*, 27:797-802 (1988).
George-Nascimento et al., "Replacement of a Labile Aspartyl Residue Increases the Stability of Human Epidermal Growth Factor", *Biochemistry*, 29:9584-9591 (1990).
Goodlad et al., "Comparison of the Mitogenic Activity of Human Epidermal Growth Factor I-53 and Epidermal Growth Factor I-48 in vitro and in vivo", *Clinical Sciences*, 91:503-507 (1996).
Goodlad et al., "Intravenous but not intragastric urogastrone-EGF is trophic to the intestine of parenterally fed rats", *Gut*, 28:573-582 (1987).
Gregory et al., "The Contribution of the C-terminal Undecapeptide Sequence of Urogastone-Epidermal Growth Fator to its Biological Action", *Regulatory Peptides*, 22:217-226 (1988).
Guglietta et al., "Clinical applications of epidermal growth factor", *Eur. J. Gastroenterol. Hepatol.*, 7(10):945-950 (1993).
Guglietta et al., "Effect of h-EGF and h-EGF 1-48 on histamine-stimulated gastric acid secretion in rats and monkeys", *J. Physiol Paris*, 87:343-347 (1993).
Hayashi et al., "A Sensitive Enzyme Immunoassay for Human Epidermal Growth Factor. Determination of HEGF in Human Serum and Urine and Pharmacokinetics in Mouse", *J Pharmacobiodyn*, 12:410-415 (1989).
Hayek et al., "Growth Factor/Matrix-Induced Proliferation of Human Adult Beta-Cells", *Diabetes*, 44:1458-1460 (1995).
Heath et al., "A synthetic approach to structure-function relationships in the murine epidermal growth factor molecule", *Proc. Natl. Acad. Sci, U.S.A.*, 83:6367-6371 (1986).
Herbst, R.S., "Review of epidermal growth factor receptor biology", *Int. J. Radiat. Oncol. Biol. Phys.*, 59(2 Suppl.):21-26 (2004).
Herbst et al., "Epidermal growth factor receptors as a target for cancer treatment: the emerging role of IMC-C225 in the treatment of lung and head and neck cancers", *Semin. Oncol.*, 29(1, Suppl. 4):27-36 (2002).
Hollenberg et al., "Epidermal Growth Factor-Urogastone: Biological Activity and Receptor Binding of Derivatives", *Molecular Pharmacology*, 17:314-320 (1980).
Jhappan et al., "TGFα Overexpression in Transgenic Mice Induces Liver Neoplasia and Abnormal Development of the Mammary Gland and Pancreas", *Cell*, 61:1137-1146 (1990).
Juhl et al., "Systemic Treatment With Recombinant Human Epidermal Growth Factor Accelerates Healing of Sclerotherapy-Induced Esophageal Ulcers and Prevents Esophageal Stricture Formations in Pigs", *Dig Dis Sci*, 39(12):2671-2678 (1994).
Keiser et al., "Hemodynamic effects of epidermal growth factor in conscious rats and monkeys", *Proc. Natl. Acad. Sci. U.S.A*, 93:4957-4961 (1996).
Kim et al., "EGF receptor signaling in prostate morphogenesis and tumorigenesis", *Histol. Histopathol.* 14(4):1175-1182 (1999).
Koch et al., "Molecular Species of Epidermal Growth Factor Carrying Immunosuppressive Activity", *Journal of Cellular Biochemistry*, 25:45-59 (1984).
Kondapaka et al., "Epidermal growth factor and amphiregulin up-regulate matrix metalloproteinase-9 (MMP-9) in human breast cancer cells", *Int. J. Cancer*, 70(6):722-726 (1997).
Konturek et al., "Release and action of epidermal growth factor on gastric secretion in humans", *Scand. J. Gastroenterol.*, 24(4):485-492 (1989).
Konturek et al., "Comparison of Organ Uptake and Disappearance Half-Time of Human Epidermal Growth Factor and Insulin", *Regul Pept*, 30:137-148 (1990).
Korc, M.J., "Islet Growth Factors: Curing Diabetes and Preventing Chronic Pancreatitis?", *Clin. Invest.*, 92:1113-1114 (1993).
Kuo et al., "Pharmacokinetic Evaluation of Two Human Epidermal Growth Factors (hEGF51 and hEGF53) in Rats", *Drug Metabolism and Description*, 20(1):23-30 (1991).
Marti et al., "Biological effects of epidermal growth factor, with emphasis on the gastrointestinal tract and liver: an update", *Hepatology*, 9:126-138 (1989).
Merchant et al., "Epidermal Growth Factor Stimulation of the Human Gastrin Promoter Requires Sp1", *J Biol Chem*, 270:6314-6319 (1995).
Merlino, G., "Epidermal growth factor receptor regulation and function", *Semin. Cancer Biol.*, 1:277-284 (1990).
Miettinen et al., "Impaired migration and delayed differentiation of pancreatic islet cells in mice lacking EGF-receptors", *Development*, 127:2617-2627 (2000).

Normanno et al., "EGF-related peptides in the pathophysiology of the mammary gland", *J. Mammary Gland Biol. Neoplasia*, 2(2):143-151 (1997).

Ohlsson et al., "Epidermal Growth Factor Induces Cell Proliferation in Mouse Pancreas and Salivary Glands", *Pancreas*, 14(1):94-98 (1997).

Patel et al., "Treatment of non-insulin-dependent diabetes mellitus", *Expert Opinion Investig Drugs*, 12(4):623-633 (2003).

Playford et al., "Epidermal Growth Factor is Digested to Smaller, Less Active Forms in Acidic Gastric Juice", *Gastroenterology*, 108:92-101 (1995).

Rehfeld et al., "The Effect of Gastrin and Cholecystokinin on the Endocrine Pancreas", *Frontiers of Hormone Research*, 7:107-118 (1980).

Robinson et al., "The international standard for epidermal growth factor (EGF): Comparison of candidate preparations by in vitro bioassays and immunoassays", *Growth Factors*, 13:163-170 (1996).

Rooman et al., "Combined gastrin and epidermal growth factor treatment induces islet regeneration and restores normoglycaemia in C57B16/J mice treated with alloxan", *Diabetologia*, 47(2):259-265 (2004).

Schally et al., "New approaches to therapy of cancers of the stomach, colon and pancreas based on peptide analogs", *Cell. Mol. Life Sci.*, 61(9):1042-1068 (2004).

Scheving et al., "Circadian phase-dependent stimulatory effects of epidermal growth factor on deoxyribonucleic acid synthesis in the tongue, esophagus, and stomach of the adult male mouse", *Endocrinology*, 105:1475-1479 (1979).

Shin et al., "Synthesis and Biological Activity of N-Terminal-Truncated Derivatives of Human Epidermal Growth Factor (h-EGF)", *Peptides*, 16(2):205-210 (1995).

Simpson et al., "Rat epidermal growth factor: complete amino acid sequence", *Eur. J. Biochem.*, 153:629-637 (1985).

Sinha et al., "Epidermal growth factor enemas are effective in the treatment of left-sided ulcerative colitis", *AGA*, pp. 55 (Abstract) (2001).

Sizemore et al., "Impact of Receptor Downregualtion on Clearance of Two Human EGFs With Different Receptor Binding Activity", *Peptides*, 17(7):1229-1236 (1996).

Slice et al., "Gastrin and EGF Synergistically Induce Cyclooxygenase-2 Expression in Swiss 3T3 Fibroblasts that Express the $CCK_2$ Receptor", *J. Cellular Physiology*, 196:454-463 (2003).

Stagsted et al., "Insulinomimetic effect on glucose transport by epidermal growth factor when combined with a major histocompatibility complex class I-derived peptide", *J. Biol. Chem.*, 268:1770-1774 (1993).

Suarez-Pinzon et al., "Combination Therapy with Epidermal Growth Factor and Gastrin Increases Beta-Cell Mass and Reverses Hyperglycemia in Diabetic NOD Mice", *Diabetes*, 54:2596-2601 (2005).

Suarez-Pinzon et al., "Combination therapy with epidermal growth factor and gastrin induces neogenesis of human islet beta cells from pancreatic duct cells and an increase in functional beta-cell mass", *J Clin Endocrinol & Metabolism*, 90(6):3401-3409 (2005).

Sullivan et al., "Epidermal growth factor in necrotizing enteritis", *Lancet*, 338(8758):53-54 (1991).

Tomioka et al., "Cellular and subcellular localization of transforming growth factor-α and epidermal growth factor receptor in normal and diseased human and hamster pancreas", *Teratogenesis, Carcinogenesis and Mutagenesis*, 15:231-250 (1995).

"Transition Therapeutics Confirms Effectiveness of Islet Neogenesis Therapy in Reducing Diabetic Symptoms", Transition Therapeutics Press Release, Apr. 17, 2002.

"Transition Therapeutics Inc. Receives Approval to Initiate Phase I Clinical Trial for Islet Neogenesis Therapy", Transition Therapeutics Press Release, Sep. 20, 2002.

"Transition Therapeutics' I.N.T.™ Treatment Stimulates Regeneration of Human Insulin-Producing Cells", Transition Therapeutics Press Release, Sep. 26, 2002.

"Transition Therapeutics' I.N.T.™ Treatment Increases Survival", Transition Therapeutics Press Release, Sep. 27, 2002.

Vinter-Jensen, L., (1996), Pharmacokinetics and Systemic Effects of Epidermal Growth Factor (EGF) with focus on the urinary and gastrointestinal tracts, *APMIS*, 93(107):1-42 (1999).

Vinter-Jensen et al., "Systemic Treatment with Epidermal Growth Factor in Pigs Induces Ductal Proliferations in the Pancreas", *Gastroenterology*, 113:1367-1374 (1997).

Von Herrath, M., "EI-INT Transition Therapeutics/Novo Nordisk", *Current Opinion Investig Drugs*, 6(10):1037-1042 (2005).

Walker-Smith et al., "Intravenous epidermal growth factor/urogastrone increases small-intestinal cell proliferation in congenital microvillous atrophy", *Lancet*, 2(8466):1239-1240 (1985).

Wang et al., "Pancreatic Duct Cells Express Gastrin and TGFα during duct to Islet-Cell Differentiation in Duct-Ligated Adult Rats", *Diabetologia*, 39(Supplement 1):A63 (Abstract) (1996).

Wang et al., "Expression of gastrin and transforming growth factor-α during duct to islet cell differentiation in the pancreas of duct-ligated adult rats", *Diabetologia*, 40:887-893 (1997).

Carpenter et al. *J. Cell. Physiol.*, 88:227-238 (1976).

Carpenter et al. in *Peptide Growth Factors*, Chapter 4, "The Epidermal Growth Factor Family" eds. Sporn and Roberts, Springer Verlag, (1990).

Gasslander et al. *Eur. Surg. Res.*, 29:142-149 (1997).

Karnes in *Gut Peptides: Biochemistry and Physiology*, Chapter 20, "Epidermal Growth Factor and Transforming Growth Factor-alpha" eds. Walsh and Dockray, Raven Press Ltd. New York (1994).

Rehfeld *Physiol. Rev.*, 78:1087-1108 (1998).

Wang et al. *J. Clin Invest.*, 92:1349-1356 (1993).

Dockray et al., "Biological Activity of Iodinated Gastrins", *Biochem. Biophys. Res. Commun.*, 69(2):339-345 (1976).

Dunbar et al., "Structure-function and biological role of batacellulin". *Int. J. Biochem. Cell Biol.*, 32:805-815 (2000).

Saillan-Barreau et al., "Evidence for a functional role of the cholecystokinin-B/gastrin receptor in the human fetal and adult pancreas", *Diabetes*, 48:2015-2021 (1999).

Wünsch et al., "Biological and immunological properties of human gastrin I analogues", *Hoppe-Seyler's Z. Physiol. Chem.*, 363:665-669 (1983).

Figure 1
Improved glucose tolerance of STZ diabetic rats after INT with Gastrin TGFα

Figure 2
Increased insulin release in INT treated rats

Figure 3 Prolonged Improvement in Glucose Tolerance to 8 weeks

Mean± SE n=8 or greater 2 weeks after Treatment          8 weeks after Treatment Figure 4 INT maintains normal fasting blood glucose levels Figure 5 INT gives sustained improvement in growth of diabetic rats for at least 8 weeks after treatment

Figure 6

Figure 7 Panel A

COMPOSITION COMPRISING A GASTRIN/CCK RECEPTOR LIGAND AND AN EGF RECEPTOR LIGAND

CROSS REFERENCE TO RELATED APPLICATIONS

This application is a continuation of application Ser. No. 10/044,048, filed Jan. 11, 2002, now U.S. Pat. No. 6,992,060, which claims the benefit of U.S. Provisional Application No. 60/261,638, filed Jan. 12, 2001. The contents of these applications are hereby incorporated by reference.

TECHNICAL FIELD

Embodiments of the invention are directed to compositions and methods for a short course of systemic treatment of diabetic patients with a gastrin/cholecystokinin (CCK) receptor ligand and an epidermal growth factor (EGF) receptor ligand, such treatment initiating pancreatic islet neogenesis when administered to subjects, and providing remission of diabetes for a prolonged period of time following cessation of treatment.

BACKGROUND

About 800,000 people in the United States population suffer from insulin deficiency diabetes (also known as juvenile or type I diabetes), and about 30,000 new cases arise each year. Further, an extremely large and rapidly increasing number of patients have forms of type II diabetes (also called adult onset or insulin-resistance diabetes), in this population at a level of epidemic proportions, that cause pancreatic exhaustion and insulin insufficiency. Diabetes type I is generally treated with insulin injection in response to blood glucose levels determined by patient glucose self-monitoring. A variety of forms of insulin, for example, slow and fast acting, and systems and devices suitable for insulin delivery by injection, for example a delivery pen, are used by the growing population of diabetics.

The abnormally high blood glucose (hyperglycemia) that characterizes diabetes, if left untreated, results in a variety of pathological conditions, for example, non-healing peripheral vascular ulcers, retinal damage leading to blindness, and kidney failure. Multiple daily doses of insulin administration by the patient, in response to frequent glucose self-monitoring per day, are required on a lifetime basis, with concomitant expense and inconvenience to the patient and the health care system. Further, greater pathological consequences of diabetes are correlated with less rigorous control of blood glucose level, control being accomplished by glucose level monitoring and insulin administration, and by dietary restrictions, so that only the compliant patients avoid negative outcomes.

Alternative diabetes therapies to glucose monitoring and insulin injection have been sought, for example, in which the diabetes patient receives a transplant of pancreatic material. These possibilities offer the potential advantage of a normal physiological response, viz., rapid release of insulin in response to increased blood glucose concentration. Transplants of allogenic or xenograft pancreatic material, such as encapsulated porcine islets or islet duct cells that have been induced to differentiate in vitro, remain experimental. Transplantation of human pancreatic material remains limited by severe insufficiency of available material and immune rejection. Transplantation of allogenic or xenograft pancreatic islet tissue remains limited because of immune rejection of the transplant, or possible transmission of an animal virus.

Transgenic mice expressing both TGFα and gastrin recombinant genes have increased pancreatic islet mass, which does not occur in mice expressing either agent alone (U.S. Pat. No. 5,885,956, issued Mar. 23, 1999 and U.S. Pat. No. 6,288,301, issued Sep. 11, 2001). Therapeutic compositions and methods for controlling blood glucose and remediating insulin insufficiency, particularly compositions and methods that can cause rapid release of insulin in response to elevated blood glucose, and that are effective for an extended period of time, remain important medical priorities.

SUMMARY OF THE INVENTION

The invention is based in part on the discovery that administration to a diabetic subject of both a gastrin receptor ligand and an EGF receptor ligand, according to a short schedule of administration of the dosages, causes islet neogenesis in the subject, and produces a response that was a surprising long term remission of the diabetic condition. The period of remission is characterized by a lowering of blood glucose, and an increase in blood insulin. No cure involving in vivo islet regeneration in a diabetic patient is currently commercially available.

In one aspect, the invention herein provides a pharmaceutical composition including a first dose of a gastrin/cholecystokinin (CCK) receptor ligand, and a second dose of an epithelial growth factor (EGF) receptor ligand. The first and second doses are in a proportion in the composition that is effective for inducing islet neogenesis in a subject in need of islet neogenesis. The gastrin/CCK receptor ligand can be, for example, a synthetic gastrin derivative. The EGF receptor ligand can be a recombinant modified EGF. For example, in one embodiment, the gastrin/CCK receptor ligand is a synthetic gastrin derivative having a leucine substituted at position 15, and the EGF receptor ligand is a recombinant modified EGF having a deletion of two C-terminal amino acids and having a neutral amino acid substituted at position 51. The subject in need of islet neogenesis can be a patient with diabetes. The diabetes can be, for example, insulin-dependent diabetes, for example, adult-onset diabetes.

In general, the first dose can be at least about equivalent by weight to the second dose in the composition. For example, the first dose is between about 2-fold and about 100-fold greater by weight than the second dose. In one embodiment, the first dose is between about 2-fold and about 10-fold by weight greater than the second dose. Alternatively, the first dose is between about 10-fold and about 100-fold by weight greater than the second dose. Specifically, the first dose can be about 0.1 microgram to about 1.0 microgram per kg body weight of the subject per day. Alternatively, the first dose can be about 1.0 microgram to about 10 micrograms per kg body weight of the subject per day; the first dose can be about 10 micrograms to about 100 micrograms per kg body weight of the subject per day; or the first dose can be about 100 micrograms to about 3.0 milligrams per kg body weight of the subject per day. In some embodiments, the dose per day (or 24 hour period) is divided among a plurality of administrations per day.

In general, the subject is a mammal. For example, the mammal is a rodent or a primate, for example, the subject is a human.

In one embodiment, the invention provides a pharmaceutical composition including a synthetic gastrin derivative and a recombinant modified EGF. The ratio of the gastrin derivative to the recombinant modified EGF is about 60:1. Yet another embodiment is a pharmaceutical composition having a synthetic gastrin derivative having a leucine substituted at position 15, and a recombinant modified EGF having a deletion of two C-terminal amino acids and a neutral amino acid substituted at position 51, wherein the ratio of the gastrin derivative to the modified EGF is about 60:1. Yet another embodiment can be a pharmaceutical composition for islet neogenesis therapy (I.N.T.™), having an effective dose of at least about 1 μg/kg body weight of a modified recombinant EGF and at least about 30 μg/kg body weight of a synthetic gastrin derivative. Yet another embodiment is a pharmaceutical composition for I.N.T.™, having an effective dose of at least about 1 μg/kg body weight of a recombinant modified EGF having a deletion of two C-terminal amino acids and a neutral amino acid substituted at position 51, and at least about 30 μg/kg body weight of a synthetic gastrin derivative having a leucine substituted at position 15.

In another aspect, an embodiment of the invention provides a method for treating a subject having diabetes, including: administering for a duration of treatment a composition having a first effective dose of a gastrin/CCK receptor ligand and a second effective dose of an EGF receptor ligand, the first and second effective doses being suitable for inducing islet neogenesis in a subject in need of islet neogenesis, and causing a period of remission which is at least about four-fold greater than the duration of treatment. The composition can be effective in increasing blood insulin and reducing blood glucose for the period of remission. For example, if the subject is a human, the duration of treatment is less about than about 0.1 percent of the average human life span which is about 70-75 years, that is, the duration of treatment is less than about one month of treatment. Alternatively, the duration of treatment is less about than about 0.2 percent of the average human life span; or the duration of treatment is less than about than about 0.3 percent of the average life span. Further, the period of remission is at least about 0.5 percent of the average human life span; the period of remission is at least about one percent of the average human life span; or the period of remission is at least about two percent of the average human life span. The method in various embodiments includes repeating administering the composition at a time corresponding to about the end of the period of remission.

Yet another embodiment of the invention provides a method for treating a subject having insulin-dependent diabetes, including: administering a dose of each of a synthetic gastrin derivative and a recombinant modified EGF for a term of treatment which is shorter in duration than about one percent of an average lifespan of the subject species, the treatment resulting in increased insulin production and decreased blood glucose; and repeating administering the composition at a time corresponding to about the end of the remission, thereby treating the subject having insulin-insufficient diabetes.

Yet another aspect of the invention provides a method for treating a subject having insulin-insufficient diabetes, including: administering a dose of each of a synthetic gastrin derivative having a leucine substituted at position 15, and a recombinant modified EGF having a deletion of two C-terminus amino acids and having a neutral amino acid substituted at position 51, for a term of treatment which is shorter in duration than about one percent of an average lifespan of the subject species, the treatment resulting in increased insulin production and decreased blood glucose; and repeating administering the composition at a time corresponding to about the end of the remission, thereby treating the subject having insulin-insufficient diabetes.

Yet another aspect of the invention provides a method of treating a diabetes patient in need of islet neogenesis, including: administering to the patient a composition having a first effective dose of a gastrin/CCK receptor ligand and an a second effective dose of an EGF receptor ligand, the composition being administered according to a dosing schedule of short duration; monitoring the blood glucose level in the patient following administering the composition; and reiterating administering of the composition to the patient when an increase in blood glucose level in the sample indicates that the patient is in need of further islet neogenesis, such that the diabetes patient in need of islet neogenesis is treated. Accordingly, administering the composition causes increased blood insulin and decreased blood glucose. The duration of the dosing schedule is less than about three months; for example, the duration of the dosing schedule is less than about two months; for example, the duration of the dosing schedule is less than about one month. Further, monitoring the blood glucose level is less frequent than about once daily; for example, monitoring the blood glucose level is less frequent than about once weekly. Monitoring the blood glucose level can be self-monitoring by the patient. Reiterating administering the composition can be less frequent than about once per six months. Alternatively, reiterating administering the composition can be less frequent than about once per year; or reiterating administering the composition can be less frequent than about once per two years. In a related embodiment, the first effective dose of a gastrin/CCK receptor ligand in the composition is at least about ten-fold greater by weight than the second effective dose of the EGF receptor ligand.

In yet another aspect, the invention provides a method of treating a diabetes patient in need of islet neogenesis, including: administering to the patient a composition having a synthetic gastrin derivative and a modified recombinant EGF, such that islet neogenesis is initiated and blood glucose is substantially reduced, the composition being administered according to a dosing schedule of less than about two months duration; monitoring the blood glucose level at intervals of less than about once per day; and reiterating administering the composition to the patient less frequently than about once per six months.

In yet another aspect, the invention provides a method of treating a diabetes patient in need of islet neogenesis, including: administering to the patient a composition including a synthetic gastrin derivative, the gastrin derivative having a leucine at position 15, and a recombinant modified EGF, the modified EGF having a deletion of two amino acids at the C-terminus and a neutral amino acid at position 51, such that islet neogenesis is initiated and blood glucose is substantially reduced, the composition being administered according to a dosing schedule of less than about two months duration; monitoring the blood glucose level in a blood sample taken at intervals of less than about once per day; and reiterating administering the composition to the patient less frequently than about once per six months.

In yet another aspect, the invention provides a method of reducing insulin usage in an insulin-deficient diabetic patient, the method including: administering an effective dosage of an I.N.T.™ composition, to induce islet neogenesis; and reducing delivery of insulin as islet neogenesis is induced, thereby causing increased insulin secretion and decreased blood glucose. In a related embodiment, the composition comprises a gastrin/CCK receptor ligand and an EGF receptor ligand. The composition can have a gastrin/CCK receptor ligand in an amount that is at least about 10-fold greater in weight than an amount of an EGF receptor ligand in the composition. Administering the composition is performed according to a schedule less than about six months in duration. Further, reducing insulin delivery can be initiated after cessation of administering the composition. Alternatively, reducing exogenous insulin dosing can be initiated within the duration of the schedule of administering the composition. Thus, insulin delivery after administering the composition is reduced to less than about 70% compared to usage in the diabetic patient before administering the composition. For example, insulin delivery after administering the composition is reduced to less than about 50% compared to usage in the diabetic patient before administering the composition; or insulin delivery after administering the composition is reduced to less than about 10% compared to usage in the diabetic patient prior to administering the composition; or insulin delivery after administering the composition is reduced to less than about 1% compared to usage in the diabetic patient prior to administering the composition.

Yet another aspect of the invention provided is a method of reducing insulin usage in an insulin-dependent diabetic patient, the method including: administering an effective dosage of a gastrin/CCK receptor ligand and an effective dosage of an EGF receptor ligand in a proportion of at least about 10:1; and reducing insulin delivering following onset of reduction of blood glucose in the patient.

An embodiment of the invention herein provides a method of increasing islet neogenesis in a patient, including administering over a term of short duration a gastrin/CCK receptor ligand and an EGF receptor ligand, such that islet neogenesis is increased.

An embodiment of the invention herein provides a kit including a gastrin/CCK receptor ligand and an EGF receptor ligand. For example, the gastrin/CCK receptor ligand and the EGF receptor ligand are combined in a single container. The kit can contain an instruction manual or a set of instructions. Further, the gastrin/CCK receptor ligand and the EGF receptor ligand can be present as unit dosages. The kit can further include insulin.

Other features and advantages of the invention will be apparent from the following description of the preferred embodiments thereof, and from the claims.

BRIEF DESCRIPTION OF THE DRAWINGS

FIG. 2 is a bar graph showing increased insulin release in I.N.T.™ treated rats 15 and 30 min following a glucose challenge. The left set of three bars each drawn as empty bars, stippled bars, and solid bars show plasma insulin levels (ng/ml) in each of the three STZ diabetic rats as in FIG. 1. The insulin levels in the non-diabetic rat group at 15 and 30 min following challenge is shown in the bars on the right, on a different scale. The data show that diabetic rats administered the I.N.T.™ treatment at the high I.N.T.™ dosage of FIG. 1 produce more than three-fold greater insulin than untreated diabetic rats at 15 and 30 min after the challenge, and that rats receiving the low I.N.T.™ dosage of FIG. 1 make more than four-fold more insulin than untreated diabetic rats at 30 min.

FIG. 7A is a bar graph showing fasting plasma insulin C peptide concentrations and fasting blood glucose concentrations. FIG. 7B is a bar graph showing pancreatic insulin content and β cell mass determined morphometrically. Insulin dependent STZ diabetic rats (BW>300 g) were treated by subcutaneous continuous infusion for two weeks with a synthetic human gastrin derivative, gastrin 17 (Leu 15), 270 μg/kg per day, and with recombinant human EGF 1-51gln51, 227 μg/kg per day, or with a Vehicle control. Each bar show mean +/−SE, for each group of 6 animals. * denotes p<0.05 (Student's t test, unpaired).

DETAILED DESCRIPTION OF THE EMBODIMENTS

The present application is related to U.S. Pat. No. 5,885, 956, filed Dec. 14, 1992 and issued Mar. 23, 1999, and U.S. Pat. No. 6,288,301 issued Sep. 11, 2001, all of which are hereby incorporated by reference herein.

As used herein, the term "gastrin/CCK receptor ligand" encompasses compounds that stimulate the gastrin/CCK receptor such that when EGF receptors in the same or adjacent tissue or in the same individual are also stimulated, neogenesis of insulin-producing pancreatic islet cells is induced. Examples of such gastrin/CCK receptor ligands are given in U.S. Pat. No. 6,288,301 issued Sep. 11, 2001, and include various forms of gastrin, such as gastrin 34 (big gastrin), gastrin 17 (little gastrin), and gastrin 8 (mini gastrin); various forms of cholecystokinin such as CCK 58, CCK 33, CCK 22, CCK 12 and CCK 8; and other gastrin/CCK receptor ligands that demonstrate the same synergistic activity with EGF receptor ligands, and which can induce differentiation of cells of mature pancreas to form insulin-secreting islet cells, when acting synergistically with an EGF receptor ligand.

Small forms of gastrin such as gastrin 17 are economically prepared by peptide synthesis, and the synthetic peptides are commercially available. Synthetic human gastrin 17, and derivatives such as human gastrin 17 having methionine substituted for leucine at position 15 are also available from Bachem AG, Bubendorf, Switzerland, and from Researchplus.

Gastrin/CCK receptor ligands include also active analogs, fragments and other modifications of the above ligands. Such ligands also include compounds that increase the secretion of endogenous gastrins, cholecystokinins or similarly active peptides from sites of tissue storage. Examples of these are omeprazole which inhibits gastric acid secretion, and soya bean trypsin inhibitor which increases CCK stimulation.

As used herein, the term "EGF receptor ligand" encompasses compounds that stimulate the EGF receptor such that when gastrin/CCK receptors in the same or adjacent tissue or in the same individual are also stimulated, neogenesis of insulin-producing pancreatic islet cells is induced. Examples of such EGF receptor ligands include full length EGF which is EGF1-53, and further include EGF1-48, EGF1-49, EGF1-52, and fragments and active analogs thereof. Other examples of EGF receptor ligands are TGFα forms that include 1-48, 1-47, 1-51, and amphiregulin and pox virus growth factor as well as any EGF receptor ligands that demonstrate the same synergistic activity with gastrin/CCK receptor ligands. These include active analogs, fragments and modifications of the above. For further background, see, Carpenter and Wahl, Chapter 4 in Peptide Growth Factors (Eds. Sporn and Roberts), Springer Verlag, 1990.

EGF has mitogenic activity, i.e., it stimulates the growth of various cells and tissues (Karnes supra; Carpenter, G. et al. *J. Cell Physiol* 88, 227-237, 1976; Gasslander, T. et al. *Eur. Surg. Res.* 29, 142-149, 1997). EGF is also found to have a cytoprotective effect, stimulating migration of a cell toward a wound in vivo, or toward a gap introduced in a monolayer of cells in culture, to promote wound healing. These biological activities are specific to a family of structurally related growth factors, including EGF, TGFα, amphiregulin and heparin binding EGF-like growth factor (Karnes, supra). The members of this family of growth factors have identical amino acids at 11 residues of the amino acid sequence, six of which are cysteine residues that form disulfide bonds.

The group of compounds which are EGF receptor ligands further includes "modified EGF", which are variants of normal or wild type EGF. Modifications have been shown to affect one or more biological activity such as the rate of clearance of EGF. The term includes peptides having the an amino acid sequence substantially similar to that of human EGF, for example, with one or a few amino acid substitutions at various residue positions.

Recombinant EGF forms have been genetically engineered to have alterations in structure and activities, for example, EGF having a methionine at position 21 replaced by a leucine residue has been described (U.S. Pat. No. 4,760,023). Recombinant human EGF (hEGF) having 51 residues, i.e., lacking the two C-terminal residues at positions 52 and 53 of hEGF, and having a neutral amino acid substitution at position 51, retain EGF activity and are more resistant to protease degradation during a microbial production process, and following administration to a subject. A series of nucleic acid molecules have been described that encode a family of proteins that have significant similarity to EGF and TGFα (WO 00/29438). EGF muteins (mutated EGF) having histidine at residue 16 replaced with a neutral or acidic amino acid have been described (WO 93/03757), such forms retaining activity at low values of pH. Chemical analogues and fragments of EGF and TGFα retain ability to bind various members of the EGF receptor family (U.S. Pat. No. 4,686,283). Various modifications of EGF or TGFα confer advantageous properties affecting one or more of recombinant protein production, in vitro and in vivo stability, and in vivo activity. A preferred recombinant modified EGF receptor ligand of the embodiments herein retains substantially full I.N.T.™ activity, and has in vivo and/or in vitro stability that is that is at least about as great or greater than normal or wild type hEGF.

A principal aspect of the invention is a method for treating diabetes mellitus in an individual in need thereof by administering to the individual a composition including a gastrin/CCK receptor ligand and an EGF receptor ligand, each in a sufficient amount and in proportion to each other so that the combination of these ligands effects differentiation of pancreatic islet precursor cells to mature insulin-secreting cells, a process known as islet neogenesis. The cells that differentiate are latent islet precursor cells that are present in the pancreatic duct of the mature animal subject. See U.S. Pat. No. 5,885,956, issued Mar. 23, 1999.

The term "mature" as used herein refers exclusively to a post-natal animal, to distinguish the mature animal from a fetal animal. Mature refers to a mammal of chronological age older than 5% of the average lifespan of the species of mammal. This term is unrelated to a stage of the subject's development or to a time of onset of diabetes. In one embodiment, the methods and compositions herein are useful for treating a patient having type I diabetes mellitus, i.e., a form of diabetes characterized by insulin dependency including insulin absence or deficiency, and referred to as "juvenile" diabetes. The method and compositions herein are useful also for treatment of patients with insulin-dependent type II, or adult-onset diabetes, for example, who produce insuffient insulin to maintain blood glucose levels due to pancreatic exhaustion.

One embodiment of a method herein comprises administering, preferably systemically, a composition which is differentiation regenerative amount of a gastrin/CCK receptor ligand, for example, gastrin, and an EGF receptor ligand, for example, EGF or TGFα, to the individual. The gastrin is synthetic, for example, synthetic human gastrin, for example, human gastrin 17, for example, having leucine at residue 15. The EGF receptor ligand is hEGF, for example, recombinantly produced EGF, for example, a recombinant modified EGF, for example, EGF produced recombinantly from a synthetic gene carrying modifications, such as a deletion of two C-terminal amino acids at positions 52 and 53, and encoding an EGF having a length of 51 amino acids. Further EGF modification can include one or more of a variety of substitutions, such as a substitution of a neutral amino acid at position 51 rather than the normal residue at position 51 of hEGF, which is the charged amino acid glutamic acid. A neutral amino acid as defined herein is one that is uncharged at physiological pH, and is preferably hydrophilic, such as by substitution of serine, alanine, and glutamine for the residue normally found at that position.

In another embodiment, the invention relates to a method for effecting the differentiation of pancreatic islet precursor cells of a subject, for example, a mammal, by stimulating such cells with a combination of a gastrin/CCK receptor ligand, for example, a gastrin such as gastrin 17, for example, synthetic gastrin 17 carrying leucine at position 15, and an EGF receptor ligand, for example, a TFGα, or a recombinant modified EGF, according to a particular dosing schedule.

As used herein, a dosing schedule refers to a protocol for administering an I.N.T.™ composition, and includes the amount of the composition delivered per day, and the duration or period of time over which the composition is administered.

Most insulin dependent diabetic patients require insulin injection at least on a daily basis. Multiple doses per day of insulin are required under certain circumstances of illness or diet for management of diabetes, and the insulin administration is indicated by results of frequent glucose monitoring, another activity which is required of a diabetes patient for optimal management of the disease, which is performed for example as often as five times daily.

In contrast, the compositions and methods herein are used for a dosage schedule of short duration, for example, a dosage period of less than 0.5 percent, or 0.2 percent, or 0.1 percent of a subject species' average lifespan.

Administration over a short duration dosing schedule of the compositions herein is followed by an extended period of efficacy, even complete remission of disease symptoms. Lifespan data used herein include: an average lifespan of a rodent in captivity of about 2.5 years (30 months); an average lifespan of a primate that is a macaque such as a cynomolgus monkey (*Macaca fascicularis*) in captivity of about 30 years (360 months); an average lifespan of a primate that is a chimpanzee (*Pan troglodytes*) in captivity of about 45 years (540 months); and an average lifespan of a primate that is a human of about 70-75 years (840-900 months). It is recognized that an average lifespan of a species varies with conditions that are cultural, such as diet, and/or genetic.

The short term of duration of the dosage schedule for a rodent such as a rat is calculated herein as, for example, equal or less than about 28 days, about 18 days, or less than about 9 days. The duration of a dosage schedule for a primate, for example, a cynomolgus monkey, a chimpanzee or a human, is longer than for a rodent, e.g., the treatment period is less than about one year, less than about three months, less than about two months, or even less than about one month.

The short term of duration of the dosage schedule for a human patient represents and even smaller percentage of the lifespan. For example, a four week duration of treatment is 0.11% of a lifespan of 70 years (3640 weeks); a two week treatment is 0.05% of the lifespan. Efficacy of the treatment extends to a period of 26 weeks (0.7%), or 52 Weeks (1.4%), or 104 weeks (2.86%).

As a result of administration of the I.N.T.™ compositions provided herein according to a dosage schedule of such short duration, the process of islet neogenesis is initiated. Precursor cells in the subject are induced to differentiate, and the differentiating cells then mature into islet cells capable of secreting insulin in response to fluctuations in blood glucose levels, i.e., a subject with diabetes enters a period of remission characterized by a normal response to a blood glucose challenge. As a result of this administration, remission of diabetes is initiated, so that the standard dosage of insulin given to a diabetic patient prior to therapy is reduced, as determined by the level of blood glucose obtained by monitoring, for example, by self-monitoring by the patient, during and following treatment. Remission from diabetes due to successful islet neogenesis therapy is indicated by a decreased fasting blood level of glucose, and by a decreased level and duration of elevated blood glucose in response to a dietary challenge of sugar consumption. Upon achieving successful islet neogenesis, insulin administration is reduced from, for example, five injections to two injections per day; from two injections to one injection per day; and from one to none, as indicated by data obtained from monitoring blood glucose levels. One of ordinary skill in the art of pharmacology, when treating a diabetic patient, is familiar with adjusting insulin dosage to levels of blood glucose following fasting and under other physiological conditions.

Dosages of the I.N.T.™ compositions to be administered to a subject are adjusted for known variations from species to species in standard data encompassing criteria for absorption, distribution, half-life kinetics in circulation, metabolism, excretion, and toxicology of the receptor ligands of the embodiments herein, for example, for each primate and rodent species. In general, dosages are adjusted to be about 100-fold greater for administration to a rodent species than to a primate species. For example, a dose of an I.N.T.™ composition for a rat is exemplified by about 3,000 μg/day of a gastrin/CCK receptor ligand and about 100 μg of an EGF receptor ligand, administered for example in three injections per day (for a total of about 9,000 μg of gastrin/CCK receptor ligand and about 300 μg of EGF receptor ligand per day), on a per kg of body weight basis. For a primate such as a cynomolgus monkey, a chimpanzee, or a human, the comparable dose is, for example, about 1 to about 3 μg of EGF receptor ligand, or about 3 to about 10 μg of EGF receptor ligand per kg body weight, and about 30 to about 90 μg, or about 90 to about 300 μg of gastrin/CCK receptor ligand per kg body weight, such daily doses to be administered as a total bolus given once per day, or divided into subdoses to be administered in two or administrations per day.

Modes of administration of the receptor ligands include but are not limited to subcutaneous, transdermal, intramuscular, intraperitoneal, intravenous, intranasal, and oral routes. The compounds may be administered by any convenient route, for example by infusion or bolus injection, by pump, by absorption through epithelial or mucocutaneous linings (e.g., oral mucosa, rectal and intestinal mucosa, etc.). The receptor ligands herein may be administered in combination with one or a plurality of other biologically active agents. Administration is preferably systemic.

The present invention also provides pharmaceutical compositions. Such compositions comprise a therapeutically effective amount of a therapeutic, and a pharmaceutically acceptable sterile carrier or excipient. Such a carrier includes but is not limit to saline, buffered saline, dextrose, water, glycerol, ethanol, and combinations thereof. The formulation should suit the mode of administration.

The composition, if desired, can also contain minor amounts of wetting or emulsifying agents, such as Tween, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc.

Various delivery systems are known and can be used to administer a therapeutic of the invention, e.g., encapsulation in liposomes, microparticles, microcapsules and the like.

In a preferred embodiment, the composition is formulated in accordance with routine procedures as a pharmaceutical composition adapted for intravenous administration to human beings. Compositions for intravenous administration are typically solutions in sterile isotonic aqueous buffer. Where necessary, the composition may also include additional components, for example, a solubilizing agent. Generally, the ingredients are supplied either separately or premixed in unit dosage form. In addition to solution form, the composition can be supplied as a dry lyophilized powder, or as a non-aqueous concentrate, for example, in a hermetically sealed container such as an ampoule or sachette indicating the quantity of active agent. Where the composition is to be administered by infusion, it can be dispensed using an infusion bottle containing sterile pharmaceutical grade water or saline. Where the composition is administered by injection, an ampoule of sterile water or saline for injection can be provided so that the ingredients may be mixed prior to administration.

The therapeutic agent embodiments of compositions of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of each of the therapeutic agents of the compositions herein, and their relative amount with respect to each other which will be effective in the treatment of a particular disorder or condition will depend on the nature of the disorder or condition, and can be determined by standard clinical techniques. The precise dose to be employed in a formulation depends also on route of administration, and the extent of the disease or disorder in a given patient, and should be decided according to the judgment of the practitioner and each patient's circumstances. However, suitable dosage ranges for intravenous and subcutaneous administration are generally about 0.1 microgram or one microgram, to about one milligram or three milligrams, per kilogram body weight, for example, from about 20 to about 500 micrograms of each active compound per kilogram body weight. Suitable dosage ranges for intranasal administration are generally about 0.01 pg per kg body weight, to about 1 mg per kg body weight. Effective doses may be extrapolated from dose-response curves derived from in vitro or animal model test systems. A daily dose is administered as a single dose or divided into a plurality of smaller fractional doses, to be administered several times during the day.

Suppositories generally contain active ingredient in the range of about 0.5% to about 10% by weight; oral formulations preferably contain about 10% to about 95% active ingredient by weight.

Embodiments of the invention herein also provide a pharmaceutical pack or kit comprising one or more containers filled with one or more of the ingredients of the pharmaceutical compositions of the invention, for example, a container having a unit dosage of each or both of a gastrin/CCK receptor ligand and an EGF receptor ligand. Associated with such container(s) can be a notice in the form prescribed by a governmental agency regulating the manufacture, use or sale of pharmaceuticals or biological products, which notice reflects approval by the agency of manufacture, use or sale for human administration. The pack or kit can in certain embodiments include one or more containers having insulin, to be administered during the dosing schedule prior to induction of islet neogenesis and remission from diabetes.

EXAMPLES

Example 1

Prolonged Efficacy of I.N.T.™ Compositions and Methods in Diabetic Rats

Figure 1:
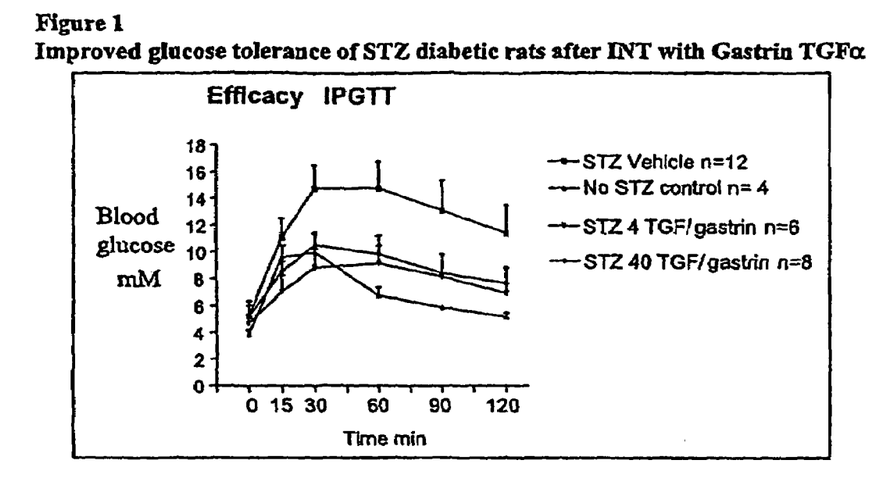
FIG. 1 is a graph showing improved glucose tolerance of STZ diabetic rats after treatment by islet neogenesis therapy (I.N.T.™) with gastrin and TGFα, as a function of time. Rat groups are non-diabetic controls (labeled No STZ control n=4, in the Figure); diabetic STZ mice treated with vehicle only (labeled STZ Vehicle n=12); rats treated with a low I.N.T.™ dosage of 4 μg of each of gastrin and TGFα per kg body weight (labeled STZ 4 TGF/gastrin n=6); and rats treated with 40 μg of each of gastrin and TGFα per kg body weight, a 10-fold higher I.N.T.™ dosage of each of gastrin and TGFα (labeled STZ 40TGF/gastrin n=8). The data show that both groups of the I.N.T.™ treated STZ rats achieved a lower blood glucose level following a challenge than diabetic rats in the untreated control group.

Diabetes was induced by intravenous injection with 50 mg/kg streptozotocin (STZ), which reduced pancreatic insulin content by 95%. One week later, STZ diabetic rats (of weight 200-250 g) were administered either the vehicle alone as a control (labeled CON in FIG. 1), or were administered a combination of human gastrin 17 (4 µg/kg) and human TGFα (4 µg/kg) peptides (labeled GAS/TGF) by once-daily, intraperitoneal injections for 12 days. At 1, 2, 4 and 8 weeks after treatment, intraperitoneal glucose tolerance tests (IPGTT) were performed, to measure both blood glucose levels, and plasma insulin levels, in response to a challenge amount of glucose.

Figure 2:
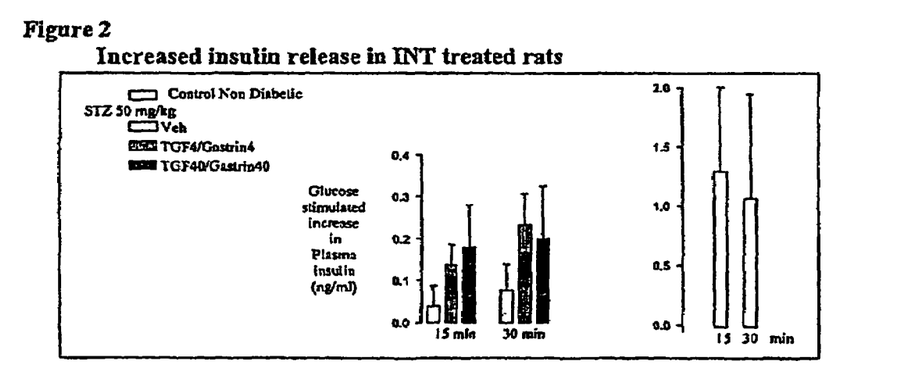

The data show that GAS/TGF treatment stimulated β islet cell neogenesis, as demonstrated morphologically by a significant increase in the number of small clusters of insulin staining cells adjacent to pancreatic ducts. Further, GAS/TGF treated rats had significantly increased pancreatic insulin concentrations compared to CON rats. At all times studied, IPGTT showed that the GAS/TGF treated rats had significantly lower blood glucose levels than the CON rats (see FIG. 1). Further, the glucose-stimulated increase in plasma insulin levels was 2-3 fold greater in the GAS/TGF treated rats compared to CON rats (FIG. 2).

Figure 3:
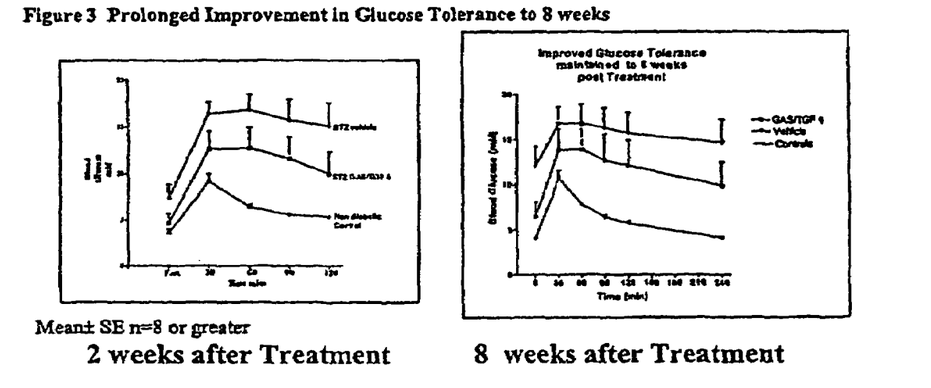
FIG. 3 is a set of graphs showing blood glucose levels for the groups of rats as in FIG. 1, assayed as a function of time, in blood samples taken two weeks after treatment (left panel) and eight weeks after treatment (right panel). The data show that blood glucose in the low dose I.N.T.™ treated rats remains lower than in untreated controls following a glucose challenge for at least eight weeks following treatment.
Figure 4:
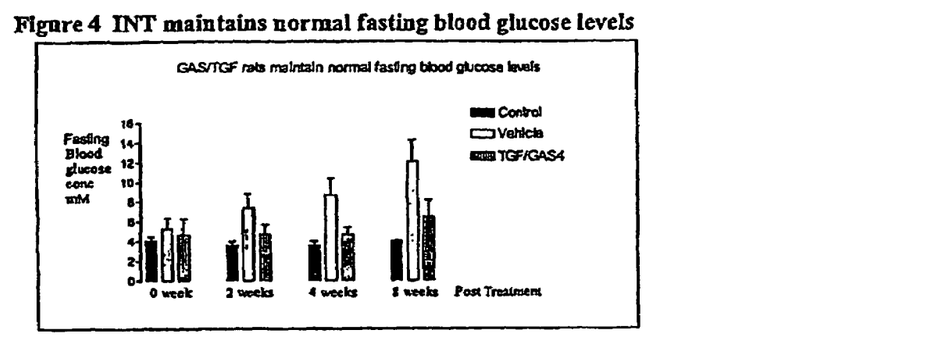
FIG. 4 is a bar graph showing fasting blood glucose concentration, in mM, in non-diabetic rats (labeled Control), diabetic untreated rats (labeled Vehicle), and rats administered low dosage I.N.T.™ treatment (labeled TGF/GAS4), at two, four and eight weeks following treatment. Data show that the I.N.T.™-treated rats remain capable of maintaining normal fasting blood glucose levels for at least eight weeks following treatment.
Figure 5:
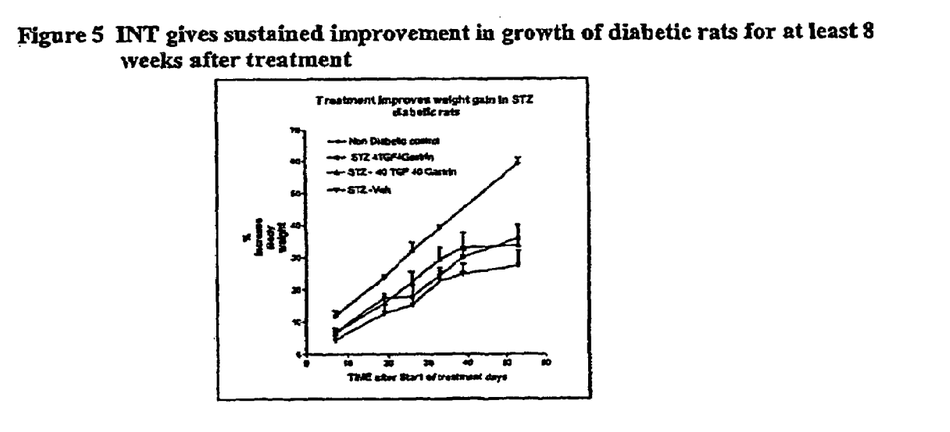
FIG. 5 is a graph showing sustained improvement in growth of diabetic I.N.T.™-treated rats for at least eight weeks following treatment, compared to untreated diabetic control rats.

Surprisingly, prolonged efficacy of the treatment was observed, with improved glucose tolerance in response to a glucose challenge in the GAS/TGF rats maintained at least to 8 weeks after cessation of treatment (FIG. 3). Further, 8 weeks after cessation of treatment, the GAS/TGF treated rats also displayed normal fasting blood glucose levels (6.4±1.2 mM) compared to the diabetic levels (12.0±2.2 mM) observed in the CON rats (see FIG. 4). Rat growth in the I.N.T.™-treated groups was normal (FIG. 5). The improved glucose tolerance correlated with improved body weight gain by the GAS/TGF group during the 8 week post treatment period.

Figure 6:
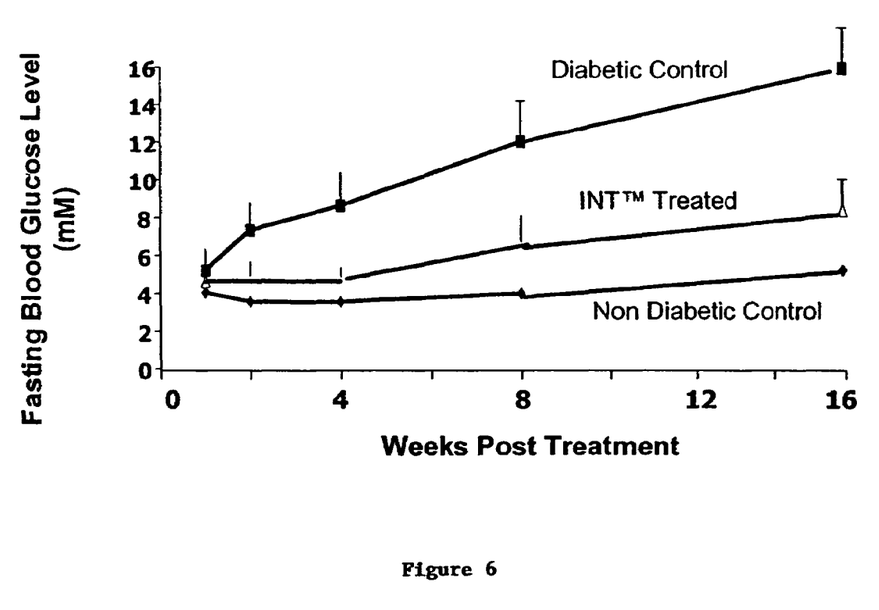
FIG. 6 is a graph showing fasting blood glucose levels of diabetic rats (labeled Diabetic Control), non-diabetic untreated rats (labeled Non-diabetic Control), and rats administered low dosage I.N.T.™ treatment (labeled TGF/GAS4), as function of time after treatment (2, 4, 8 and 16 weeks). Data show that I.N.T.™-treated rats maintain a lower fasting blood glucose level at least for 16 weeks following treatment, compared to untreated diabetic control rats

Further, additional data indicate that efficacy of the I.N.T.™ treatment continues to at least 16 weeks after cessation of the treatment (FIG. 6).

Example 2

Treatment by Subcutaneous Administration of EGF and Gastrin in Diabetic Rates for Two Weeks Results in Increased Pancreatic β Cell Mass, Insulin Content, and Insulin Secretion, and Reduced Blood Glucose in Diabetic Rats Diabetic STZ rats were prepared as above, using rats of body weight greater than 300 g. These were treated with EGF and gastrin by subcutaneous administration (subcutaneous continuous infusion), as follows. Rats were treated for two weeks with synthetic human gastrin 17 (Leu 15), 270 µg/kg per day and recombinant human EGF 1-51 gln 51, 227 µg/kg per day, or with Vehicle control. Each bar show mean +/−SE for 6 animals, and * denotes p<0.05 (Student's t test, unpaired). Pancreatic insulin was determined by immunoassay, and β cell mass was determined by point counting morphometric analysis of pancreatic histological sections after immunohistochemical staining with insulin antibodies to stain β cells. Antibody is specific for insulin C peptide.

Increased plasma insulin C peptide levels (FIG. 7A, left panel) and reduced fasting blood glucose levels were observed (FIG. 7A, right panel) were observed for the EGF/gastrin treated rats, compared to control rats receiving vehicle only.

Figure 7:
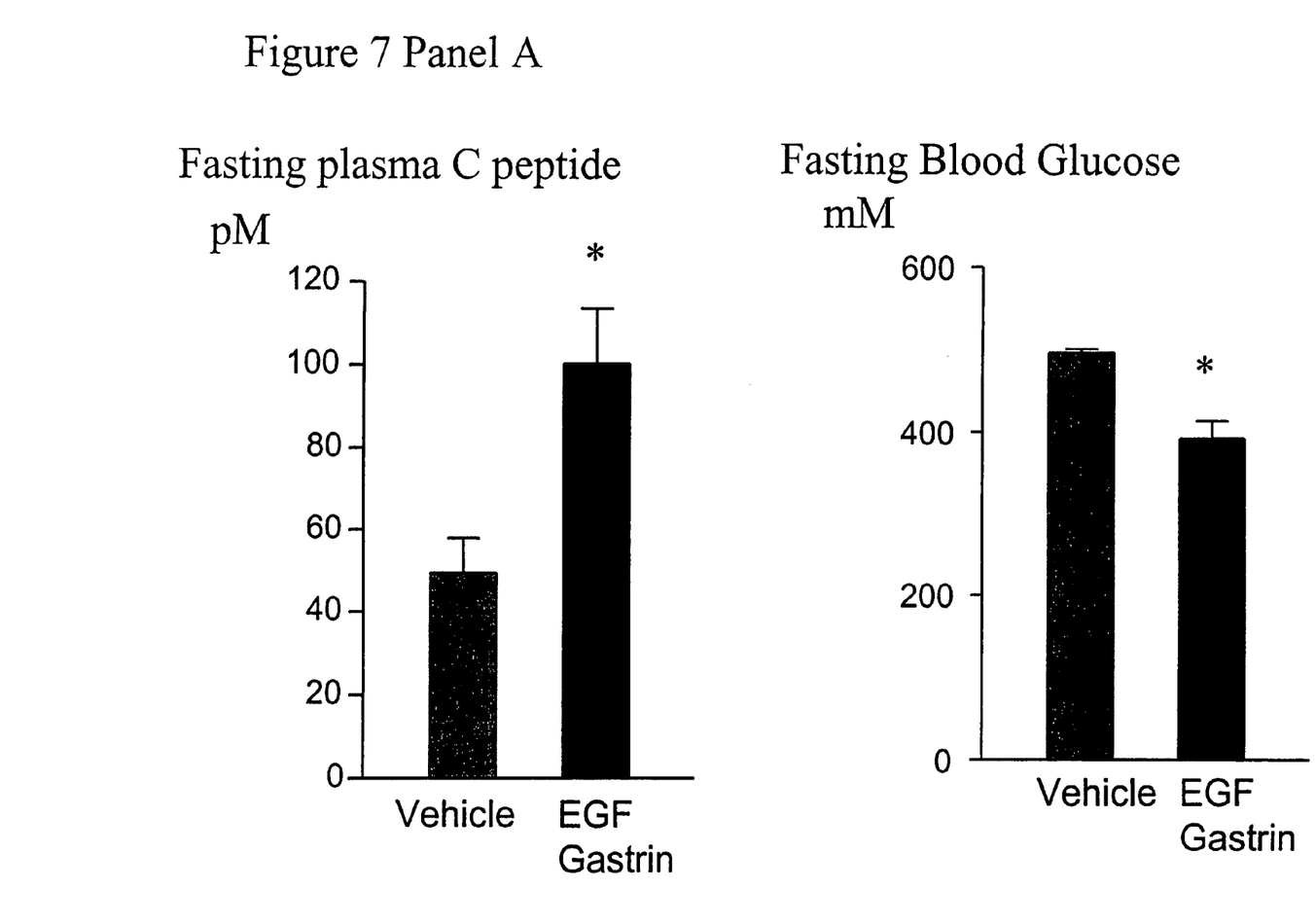

Further, rats were examined for pancreatic insulin content and number of insulin secreting pancreatic β cells (see FIG. 7, Panel B). FIG. 7B shows the pancreatic insulin content and β cell mass determined morphometrically, from the treated insulin dependent STZ diabetic rats (labeled INT) and from vehicle control (labeled Veh). Treated rats showed about three fold greater insulin content, and about two fold greater β cell mass than control rats.

Example 3

Increasing the Proportion of Gastrin in the EGF/Gastrin Combination Improved the Remission of Diabetes I.N.T.™ compositions and methods of treatment were performed using groups of STZ rats, using a dosing schedule of 28 days duration, and a composition having gastrin at a weight 30-fold greater than EGF. Rats were administered 100 micrograms/injection of the EGF receptor ligand per kg body weight, and 3 milligrams/injection of gastrin/CCK receptor ligand. Three such injections were administered per day.

Figure 8:
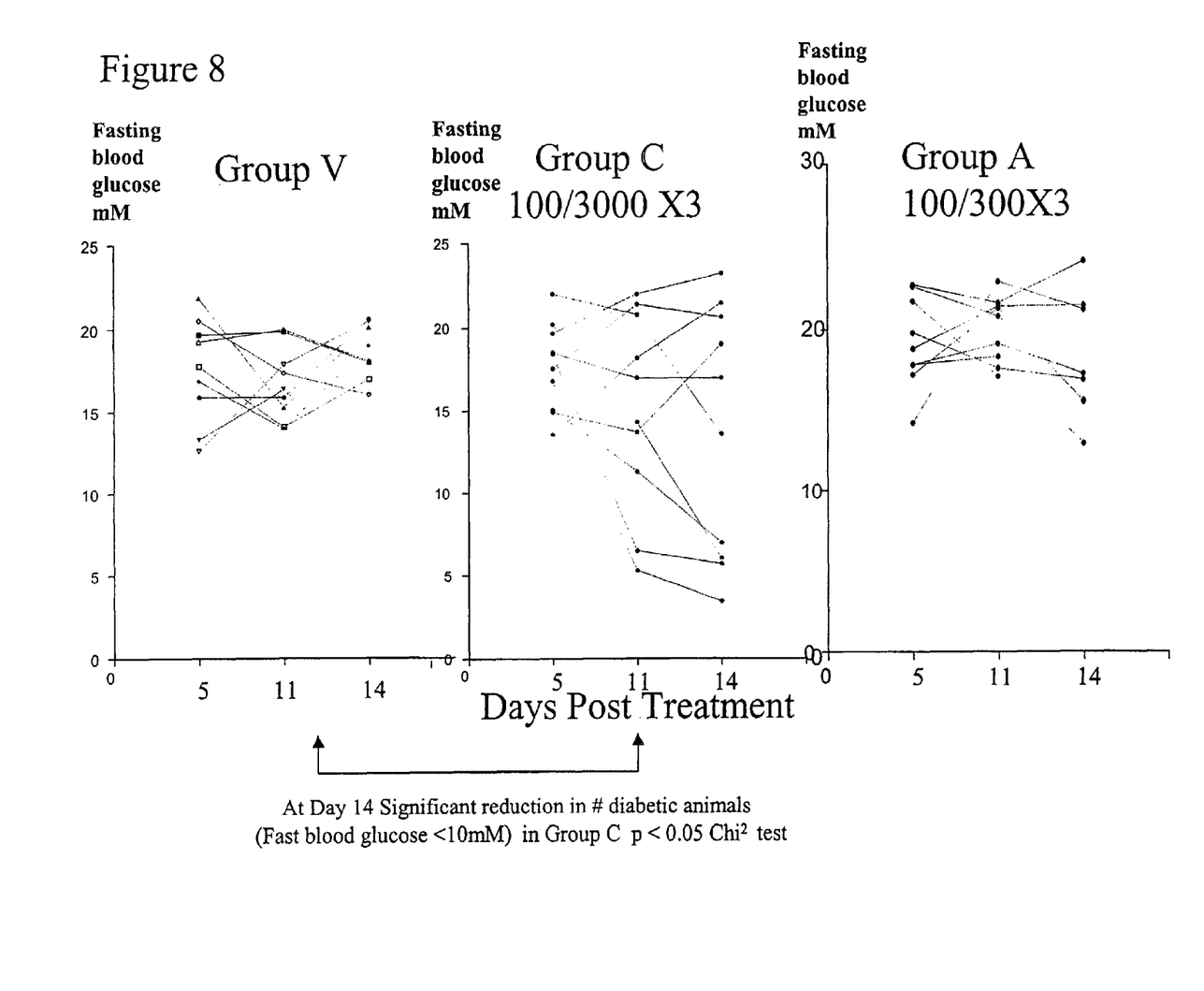
FIG. 8 is scattergram graph showing levels of fasting blood glucose concentrations from each of the STZ insulin dependent diabetic rats at 4, 11 and 14 days after completing treatment with gastrin, 300 μg/kg, and EGF, 100 μg/kg (group A); with 3,000 μg/kg gastrin and 100 μg/kg EGF (Group C); or control Vehicle (Group V), injected subcutaneously three times daily for 28 days. The number of animals showing remission of diabetes, remission indicated by having a blood glucose level of less than 10 mM at 14 days post treatment, was compared between groups by Chi squared test at a significance of p<0.05. The graph shows that at 14 days after 28 days treatment with 3000 μg/kg and EGF 100 μg/kg (group C), a significant number of animals (4 of 10) showed complete remission of diabetes compared both to the vehicle group (where none of 9 animals showed remission) and to the experimental group having a different ratio of 300 μg/kg and EGF 100 μg/kg (group A, where only one animal showed complete remission). A feature of this response is that remission was delayed 11-14 days after treatment was completed.

FIG. 8 shows the fasting blood glucose level after 28 days of treatment of diabetic rats with 3,000 μg/kg synthetic gastrin 17 Leu15, administered along with recombinant modified EGF51 Gln51 (100 μg/kg). The data show that this treatment gave a significantly greater number of rats with remission of diabetes (as defined by fasting blood glucose below 10 mM) (Group C) compared to the untreated control group (Group V). By contrast, treatment with a 300 μg/kg gastrin with the same dose of EGF (100 μg/kg) did not induce remission in a significant number of animals (Group A).

Surprisingly, within 14 days of cessation of treatment with the I.N.T. composition having a ratio by weight of gastrin/EGF of 30:1, blood glucose levels of a significant number of treated animals were observed to fall within non-diabetic levels. The 30:1 level of gastrin was important to the response since the control group of diabetic rats treated with 3:1 ratio having a 10-fold lower dose of gastrin did not show a significant number of non-diabetic animals at 14 days after treatment.

What is claimed is:

1. A pharmaceutical composition comprising a first dose of a gastrin, and a second dose of an epithelial growth factor (EGF), wherein the first dose is between about 10-fold and about 100-fold by weight treater than the second dose and the composition is effective for inducing islet neogenesis in a subject in need of islet neogenesis.

2. The composition of claim 1, wherein the gastrin is a synthetic gastrin derivative.

3. The composition of claim 1, wherein the EGF is a recombinant modified EGF.

4. The composition of claim 1, wherein the gastrin is synthetic gastrin 17 having a methionine substituted with leucine at amino acid position 15 relative to the amino acid sequence of wild type gastrin 17, and the EGF is a recombinant modified EGF1-53 having a deletion of two C-terminal amino acids at amino acid positions 52 and 53 and having a neutral amino acid substituted at position 51 relative to the amino acid seciuence of wild type EGF1-53.

5. The composition of claim 1, wherein the subject in need of islet neogenesis is a patient with diabetes.

6. The composition of claim 1 wherein the gastrin is a gastrin 34, gastrin 17 or gastrin 8.

7. The composition of claim 1 wherein the EGF is an EGF1-53, EGF1-48, EGF1-49, or EGF1-52.

8. A kit comprising a gastrin and an EGF wherein the gastrin is in a dose that is between about 10-fold and about 100-fold by weight greater than the dose of EGF.

9. The kit of claim 8 wherein the gastrin is gastrin 34, gastrin 17 or gastrin 8.

10. The kit of claim 8 wherein the EGF is an EGF1-53, EGF1-48, EGF1-49, or EGF1-52.

11. The kit of claim 8, wherein the gastrin is synthetic gastrin 17 having a methionine substituted with a leucine at amino acid position 15 relative to the amino acid sequence of wild type gastrin 17, and the EGF is a recombinant modified EGF1-53 having a deletion of two C-terminal amino acids at amino acid positions 52 and 53 and having a neutral amino acid substituted at position 51 relative to the amino acid sequence of wild type EGF1-53.

* * * * *